United States Patent [19]
Endo et al.

[11] Patent Number: 4,501,161
[45] Date of Patent: Feb. 26, 1985

[54] AUTOSAMPLER

[75] Inventors: Isao Endo, Kokubunji; Teruyuki Nagamune, Wako; Ichiro Inoue, Tokyo, all of Japan

[73] Assignee: Rikagaku Kenkyusho, Japan

[21] Appl. No.: 459,598

[22] Filed: Jan. 20, 1983

[51] Int. Cl.³ .............................................. G01N 1/14
[52] U.S. Cl. ................................ 73/863.24; 73/863.25
[58] Field of Search ........... 73/863.23, 863.24, 863.25, 73/864.34, 864.35

[56] References Cited

U.S. PATENT DOCUMENTS 3,552,211  1/1971  Dollinger et al. ................. 73/863.24
3,795,149  3/1974  Gillette ............................. 73/863.24
3,915,011 10/1975  Nelson ............................. 73/864.35
4,112,768  9/1978  Holland et al. ................... 73/863.24

Primary Examiner—S. Clement Swisher
Attorney, Agent, or Firm—Jacobs & Jacobs

[57] ABSTRACT

This invention relates to an apparatus for automatically sampling a clarified test solution from a suspension to be tested, which comprises two filtering tubes being immersed in the suspension, a circulator connected to the one tube, and a sampling cell connected to the circulator and the other tube. The suspension is sucked by the circulator and filtered through the one tube. The filtered and clarified test solution is sampled in the sampling cell and the residual test solution is returned to the suspension through the other tube. A flow direction of the test solution is reversed at intervals so that the filtering tubes are not blocked by suspending solids.

3 Claims, 3 Drawing Figures

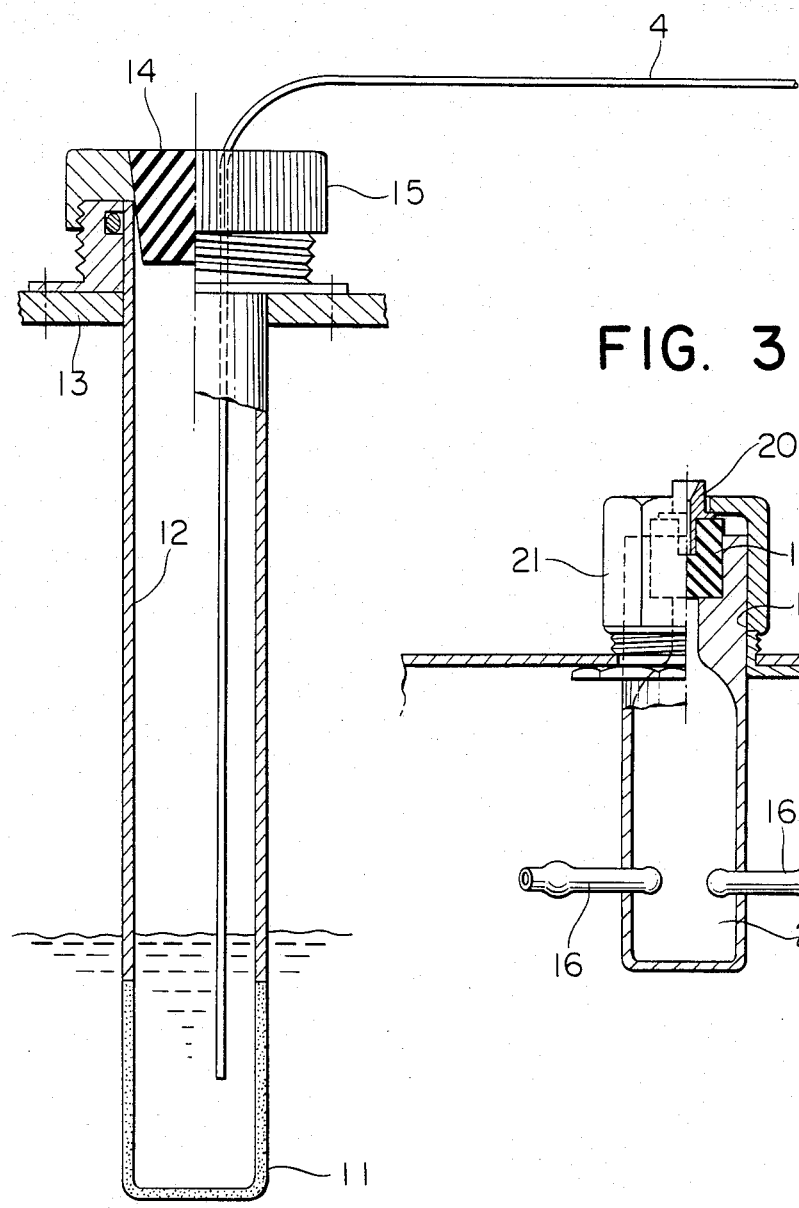

AUTOSAMPLER

BACKGROUND OF THE INVENTION

1. Field of the Invention:

This invention relates to an apparatus for sampling a clarified test solution from a suspension containing insolubles such as soilds, microorganisms and so on.

It is very important, especially in the fermentation industries, to determine such conditions as concentration of substrate, pH, composition and the like, of microbial metabolites in culture liquid in order to operate microbial metabolic reaction efficiently and to control the reaction from outside of the system.

Thus, it is very contributive to the industries to the sample automatically a clarified test solution from culture broth in order to determine above mentioned conditions.

2. Description of the Prior Technics:

Culture broth is usually a suspension which contain microbial cells and other suspending solids. Therefore, the culture broth as it is can not be used as a test solution for a gas or a liquid chromatography. So far a certain amount of culture broth has been separated therefrom, and filtered or centrifuged to obtain a clarified solution which is then used as a test solution in chromatographies. However, such solid-liquid separation process has the following disadvantages; during the process, there are possible changes in composition of the test solution (for example, as in an alcoholic fermentation) and there is a time lag between preparation of the clarified sample and determination thereof, as a result, actual concentration, pH and composition of the culture broth at a certain time may differ from those obtained by subsequent determination.

Under such circumstances, there is a technical need in the fermentation industries which enable us to remove insolubles contained in suspension and to sample the clarified solution thus obtained. If such apparatus is realized, it may be combined with many kinds of autoanalyzers and it will fortify an on-line automatic monitoring systems.

The inventors of this invention have conducted studies about such autosampler and achieved the present invention.

SUMMARY OF THE INVENTION

This invention relates to an apparatus for automatically sampling a clarified test solution from a suspension to be tested, which comprises two filtering tubes which are immersed in the suspension, a circulator connected to the one tube, and a sampling cell in which the test solution is sampled and which is connected to the circulator and the other tube, wherein the suspension is sucked by the circulator and filtered through the one filtering tube, the filtered and clarified test solution is sampled in the sampling cell, the residual test solution is returned to the suspension through the other filtering tube, and a flow direction of the test solution is reversed at intervals so that the filtering tubes are not blocked by insolubles.

One of the embodiments of this invention in which the suspension is a culture broth will now be explained with reference to the accompanying figures.

BRIEF DESCRIPTION OF THE FIGURES

FIG. 2 is a sectional view of a filtering tube which is mounted on a cover of a fermenter and FIG. 3 is a sectional view of a sampling cell.

DESCRIPTION OF THE PREFERRED EMBODIMENT

Figure 1:
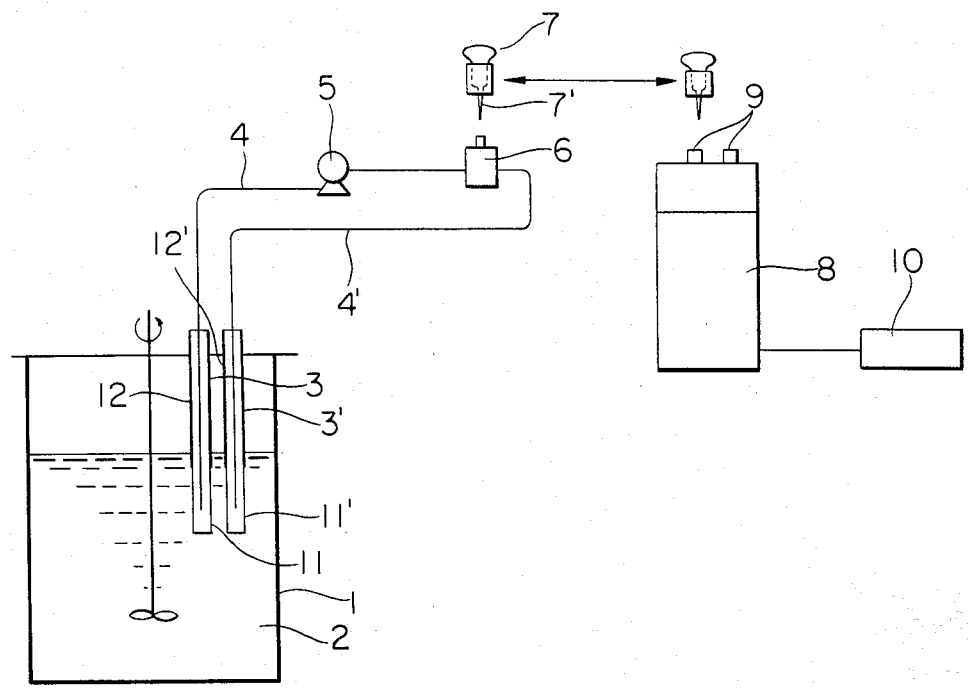
FIG. 1 is a schematic diagram of an autosampler according to the present invention connected to a gas chromatograph apparatus.

Filtering tubes 3 and 3' comprises porous or permeable parts 11 and 11' which are immersed in a suspension to be filtered therethrough, and nonporous or impermeable parts 12 and 12' which are placed above the suspension liquid level and keep the inside of the filtering tubes air-tight and liquid-tight. Porous parts 11 and 11' of the tubes 3 and 3' may be made by sintering such materials as ceramic, metal, metal alloy auch as stainless steel, synthetic resin, polymer powder, fiber, wire fabric or by treating the tubes thus sintered with a acid, a base, or a beam to make them porous. Nonporous or impermeable parts 12 and 12' may integrally be formed with porous parts 11 and 11' or may be made out of different materials from porous parts 11 and 11'. Pore size and porosity of porous parts are suitably selected depending upon particle size of suspended insolubles and porosity are usually preferred to be in the range of 10% to 40%. Pore size may be, for example, selected in the range of $1\mu$ to $10\mu$ for culture both in which microorganisms are suspended, or smaller pore size may be selected for a suspension of smaller particles.

In operation, the entire porous parts of the filtering tubes are immersed in the suspension which is then filtered through the porous part 11 and 11'. Filtered and clarified test solution whithin the tube 3 is sucked by pump 5, which lowers the pressure inside of the tube 3, consequently culture both 2 in a fermenter 1 is sucked into the tube 3 through porous part 11, while insolubles in the liquid 2 such as cells, enzymes and the like are not permitted to pass through the pore of porous part 11. Thus, insoluble solids are filtered out by porous part 11. The clarified test solution is transferred via line 4 to a sampling cell 6 by pump 5. A volume of the clarified test solution 22 in the cell 6 is suitably selected to prevent the test solution from remaining therein. The test solution is sampled in the cell 6 through a microsyringe 7', and the residual test solution flows via line 4' to the other filtering tube 3'. Since the test solution is forced to circulate by the pump 5, it is returned to a fermenter 1 through porous part 11' by a high pressure inside of the tube 3'.

According to the present invention, the test solution is sucked through not only the one tube, but also the other tube alternately. If only the one tube is used to suck the test solution therethrough, such solids as cells, complex salts or other insolubles in suspension liquid block pores of the porous part, which interferes with the suction and consequently sampling. This invention, accordingly, uses two filtering tubes, the one being washed while the other being used to suck the test solution therethrough, and the flow direction of the test solution being reversed at intervals, as a result, substantially no blocking phenomena is moderated in the present invention. For the reason that the flow direction is reversed at intervals, inlets or outlets 16 and 16' of the sampling cell are provided on the same level, as shown in FIG. 3.

As seen from the above, while the one porous part is used to filter the suspension therethrough, the other porous part is washed by the filtered and clarified test solution returning to the fermenter therethrough.

Pressure indicator such as a mercury manometer (not shown) may be connected to lines 4 and 4' to monitor blocking of the porous parts. Then, a program may be made to reverse the pump and consequently the flow direction of the test solution, when the pressure indicated exceeds the certain limit.

The clarified solution in the sampling cell 6 is sampled to analyze according to, for example, the following procedure.

A selected volume of the clarified solution in the cell 6 is sucked via a microsyringe 7' into an injection ampul 7 which is then moved to a vent 9 of a gaschromatograph apparatus into which the clarified solution in ampul 7 is automatically injected to be analyzed.

If the procedure described above is programmed, the fully automatic process from sampling to analyzing can be achieved.

Thus, according to the present invention, there are provided an apparatus for highly efficient and rapid autosampling of a claified solution from a suspension.

It should be understood that the present invention can be applied to sampling a clarified solution, which contains substantially no insoluble solids, not only from the culture broth illustrated above, but also from various chemical reaction liquid, waste water, river water, sea water, lake water and the like.

EXAMPLE

Using th apparatus shown in FIG. 1 under the conditions described below, clarified test solution was obtained. Blocking phenomena of porous parts was within the limit of and accordingly no interference with suction was occured.

Volume of Fermenter: 3 l (working volume 2 l)
Microorgansim: Brewer's yeast, Hakken No. 1 (*Saccharomyces cerevisiae*)
Medium composition: Following Table 1

Agitation speed: 450 rpm
Porous tube: sintered of stainless steel powder (SUS 316L) 70 m/m×11.5$\phi$, mean pore diameter 1u, specific gravity 5.60, specific surface area 5.59 $m^2/g$,
Suction speed: 11.4 ml/min.
Recurrent time: 5 min.

TABLE 1

| Medium Composition | | | |
|---|---|---|---|
| Asparagine | 1.5 g | Glucose | 5–100 g |
| $KH_2PO_4$ | 1.5 g | Thiamine- HCL | 0.5 mg |
| $(NH_4)_2SO_4$ | 1.5 g | Inositol | 10 mg |
| $MgSO_4 7H_2O$ | 0.5 g | Ca—pantothenate | 0.5 mg |
| $CaCl_2 2H_2O$ | 0.2 g | Pyridozine HCl | 0.5 mg |
| $FeSO_4 7H_2O$ | 0.25 mg | PABA | 0.05 mg |
| $ZnSO_4$ | 0.5 mg | Nicotinic acid | 0.5 mg |
| $CuSO_4 5H_2O$ | 0.5 mg | Biotin | 2 r |
| | | Total | 1 liter |

What we claim is:

1. An autosampler for sampling a clarified test solution from a suspension to be tested, which comprises two filtering tubes which are adapted to be immersed in the suspension, a circulator connected in series with one filtering tube, a sampling cell for sampling test solution, and the other filtering tube, the sampling cell being connected between the circulator and the other filtering tube, the circulator being operable to draw a test solution from the one filtering tube, whereby the test solution is filtered and clarified, to deliver the filtered and clarified test solution to the sampling cell, whereby the test solution is sampled, and to return the residual test solution from the sampling cell to the suspension through the other filtering tube, and said circulator being operable to periodically reverse the flow direction of the test solution so that the filtering tubes do not become blocked.

2. The autosampler as defined in claim 1, wherein a pressure indicator is provided between the circulator and each filtering tube.

3. The autosampler as defined in claim 1, wherein the suspension is a culture broth of a microorganism.

* * * * *